United States Patent [19]

Yananton

[11] 3,951,747
[45] Apr. 20, 1976

[54] LYOPHILIZED MEDIA

[75] Inventor: Patrick Michael Yananton, Garfield, N.J.

[73] Assignee: Hoffmann-La Roche Inc., Nutley, N.J.

[22] Filed: June 27, 1974

[21] Appl. No.: 483,495

Related U.S. Application Data

[63] Continuation-in-part of Ser. No. 177,478, Sept. 2, 1971, abandoned.

[52] U.S. Cl. .......................... 195/103.5 R; 195/102
[51] Int. Cl.² .......................................... C12K 1/06
[58] Field of Search..... 195/100, 101, 102, 103.5 R, 195/98

[56] References Cited
UNITED STATES PATENTS

| | | | |
|---|---|---|---|
| 2,897,600 | 8/1959 | Graham et al. | 195/98 |
| 3,107,204 | 10/1963 | Brown et al. | 195/139 |
| 3,216,907 | 11/1965 | Goldman | 195/103.5 R |
| 3,360,440 | 12/1967 | Haab et al. | 195/103.5 R |
| 3,553,082 | 1/1971 | Hach | 195/103.5 R |
| 3,704,204 | 11/1972 | Heck | 195/100 |
| 3,713,985 | 1/1973 | Astle | 195/100 |

OTHER PUBLICATIONS

Journal of Bacteriology, Vol. 77, pp. 65–69, (1959).
Hannan et al., Journal of Laboratory and Clinical Medicine, Vol. 33, pp. 1338–1341, (1948).
"Auotab", brochure by Colab Industries, Inc., Glenwood, Ill., 4/1971.
Arnold et al., J. Lab. Clin. Med., Vol. 33, pp. 1334–1337, (1948).
Cowan, J. Gen. Microbiol. Vol. 8 pp. 391–396 (1953).
Colwell et al. Canadian J. Microbiol., Vol. 8, pp. 813–816, (1962).
Lettau Zeit. Chem., 1970, Vol. 10, Heft. 12, pp. 462.

Primary Examiner—Alvin E. Tanenholtz
Attorney, Agent, or Firm—Samuel L. Welt; Jon S. Saxe; Gerald S. Rosen

[57] ABSTRACT

A method for identifying or detecting biologically active materials more rapidly and conveniently than standard identification methods involving the use of lyophilized media within microcontainers is disclosed.

5 Claims, No Drawings

LYOPHILIZED MEDIA

RELATED APPLICATIONS

This patent application is a continuation-in-part of U.S. patent application Ser. No. 177,478, filed Sept. 2, 1971 and now abandoned.

BACKGROUND OF THE INVENTION

Previously, micro methods for identifying or detecting biologically active materials involved the use of small test tubes, capillary tubes, trays and the like. The media utilized in these methods have previously been confined to liquid broths or agar gels which are prepared from commercially available powder forms. Problems inherently associated with media in the aforementioned forms are manifested in the labor of preparation, sterilization and dispersion which result in a material which lacks a commercially practical shelf-life. Macro methods involve the use of larger containers and have the same problems as associated with the micro methods.

DETAILED DESCRIPTION OF THE INVENTION

This invention is based on the discovery that the problems associated with media utilized in micro or macro methods for identifying or detecting biologically active materials are substantially overcome and unique advantages realized by the use of lyophilized media within microcontainers.

By "biologically active materials" is meant materials which have biological effects which can be measured in nutrient media and noted visually with indicators or other means. Typical materials are bacteria, bacterial enzymes, human pathogenic bacteria and the like.

The lyophilized media within microcontainers can be used for a variety of microbiological tests such as urease determination, amino acid decarboxylation or deamination, sterility testing, water testing Ortho-nitro-para-beta-D-Galactopyranoside (ONPG) test, arginine dihydrolase test, ornithine and lysine decarboxylase test, gelatin liquefaction and the like. Other substances such as inhibitors can be added directly and lyophilized with the medium permitting the preservation of serial dilutions. Examples of the uses of the tests are for identifying microorganisms such as bacteria by determining their enzymatic fermentation of various carbohydrates as well as effects of decarboxylating amino acids.

A typical clinical situation which arises frequently particularly in hospitals or diagnostic laboratories, is the identification of pathogenic organisms in human infections. Typical pathogenic organisms amenable to identification by utilization of this invention are bacteria. Of the bacteria amenable to identification, those of the family Enterobacteriaceae are typical.

Generally, in order to identify a pathogenic organism, it is incubated in various biochemical indicators. The growth or lack of growth in the media, and the biochemical responses are observed in order to obtain an activity profile of the organism. This profile is an identifying factor and can be used alone or in conjunction with other identifying means in order to determine the identity of the pathogenic organism.

The media useful in the practice of this invention, when in lyophilized form, have several distinct advantages over existing media formed by other means. The lyophilized materials have excellent storage and shelf stability, for example, a broth nutrient medium containing a carbohydrate has stability of at least three months and, in many cases, stability for over a year has been observed and refrigeration is not necessary. The use of lyophilized media prepared in micro systems is also advantageous since it is sterile, eliminates labor of preparation, stocking of media supplies and decreases storage space and the use of glassware. Small quantities are used, conserving materials, minimal amounts of inoculant are used, results are more rapid, can be adapted to mechanized methods and the system is disposable.

The media useful in this invention are formed by conventional lyophilization procedures. For example, a broth medium is sterilized in an autoclave, using standard procedures cooled and then rapidly freeze dried under vacuum. The conditions under which this is accomplished varies with the medium. The autoclave procedure must not be so severe that the components of the medium decompose or are otherwise adversely affected.

The lyophilized broth media is within microcontainers, i.e., microtubes of commercially available size, usually 13 × 100 mm., 10 × 75 mm. or 6 × 50 mm. Tubes which are 10 × 75 mm. are most preferred. Micro-trays can also be used, however, microtubes are preferred.

The organism, i.e., biologically active material to be tested is added to the lyophilized media as an aqueous suspension thus rehydrating the media. The concentration of the organism is not critical to the operability of the test but generally at least about $10^9$ organisms are utilized. This specific concentration is not required for operability but it is the concentration generally used. However, as long as some organisms are present, detectable growth occurs within 24 hours.

The amount of water utilized in the aqueous suspension containing the test organism to rehydrate the lyophilized media is sufficient to form solutions containing a predetermined concentration of ingredients. The test organisms are suspended in this water in sufficient concentration to insure that the test will give meaningful results.

When the aqueous suspension of test organism is added to the lyophilized media, the media are simultaneously instantaneously rehydrated and inoculated. This is an important advantage since it results in a considerable saving of time. The fermentation, growth or enzyme activity is then noted following incubation. The results are generally available within one to eight hours. However, for optimum results a period of about 24 hours is allowed to elapse prior to taking a final reading.

The compositions of the media used in this invention vary, of course, depending on the particular system under test. Thus, for example, a medium suitable for determining the fermentation activity profile of Enterobacteriaceae is composed of a nutrient, a carbohydrate, an indicator and water. A base or acid may be included to adjust the pH of the system.

The amounts of ingredients in the media can vary. However, an optimum concentration has been determined for each ingredient in the various media and is well known to the skilled artisan.

Thus, a broth medium usually contains optimally on a weight basis 0.5% trypticase peptone, 1% carbohydrate, 0.0018% phenol red indicator and sufficient water to make 100 ml.

If a base or acid is used to adjust the pH, usually an inorganic acid or base such as NaOH or HCl is used. The pH is adjusted to insure that the organism under test acts upon the correct ingredient in the medium to cause a pH shift which will cause the indicator to change color. In testing the activity profile of e.g., Enterobacteriaceae, a pH of about 7.3 to 7.8 is used.

The nutrient utilized can vary, depending on the bacterial-biochemical trait being tested. Thus, tryptic digest of casein and peptone, e.g., Trypticase Peptone (Baltimore Biological Laboratories) is preferred as a base for carbohydrate fermentation determination. Vegetable peptone, e.g., Phytone Peptone (Baltimore Biological Laboratories) is preferred for lysine decarboxylase and gelating peptone, e.g., Gelsate Peptone (Baltimore Biological Laboratories) is preferred for urea. Others will become obvious to those skilled in the art.

The carbohydrate or amino acids used, wherein applicable, can vary, e.g., dextrose, lactose, sucrose, mannitol, dulcitol, salicin, adonitol, inositol, sorbitol, arabinose, raffinose, ornithine, lysine, phenylalanine and the like are utilized.

The lyophilized media are inoculated with a suspension of the organisms to be tested by transferring 1 loop, i.e., 2 or 3 colonies from a culture on a bacteriological media into an amount of sterile water or saline sufficient to rehydrate the media to its composition prior to lyophilization. The concentration of bacteria should be sufficient to provide growth. $10^9$ organisms are preferably used. The dilute organism is transferred to the small test tubes containing lyophilized media (broth) with a pipette or a syringe, usually about 1 ml. is tranferred. In the case of the tray, usually 0.1 ml. is transferred with a syringe.

The inoculum size is not critical since it may take 24 hours to get completely reliable results. Hence, even one or two individual organisms are sufficient. The reason 24 hours are required for the reliable reading is that some organisms do not ferment some sugars until at least six hours have elapsed.

The identity of the indicator utilized is not critical just as long as it is compatible with the pH change occurring in a particular medium at the proper point in the growth cycle to enable it to be effective.

In conducting the various tests, it has been found that when the containers are sealed, loss of inoculated test media, and contamination, are substantially reduced, insuring meaningful results.

Conventional sealing means can be used, e.g., tape, wax, etc.

In conducting the tests, incubation of the test media is needed. Generally an incubation temperature of about 35°–38°C. is utilized. The results are usually followed visually and are considered final when the color of the indicator remains stable.

The media are also useful in macro tests for, e.g., determining bacterial contaminants in water.

The following Examples illustrate the invention.

EXAMPLE 1

Standard carbohydrate broth medium was prepared containing the following ingredients on a weight basis:

| | |
|---|---|
| 0.5% | trypticase peptone |
| 1% | carbohydrate |
| 0.0018% | phenol red indicator |
| 100 ml. | water q.s. |
| adjusted to pH 7.5 with 10% NaOH | |

The ingredients were mixed at room temperature then autoclaved at 118°C. for 15 minutes. After cooling, the medium was placed in a water bath at 50°C. and microtubes of 10 × 75 mm. length were filled with the medium. The amount of medium placed in each tube was 0.1 ml. of a 10 × concentrate. After filling, the tubes were placed in a freeze-dryer chamber preset at −40°F. After one hour at −40°F., the chamber was evacuated until a vacuum of about 100 microns or less was achieved. The chamber was then heated to 70°F. for about 24 hours. The vacuum was broken and the tubes were removed. The tubes containing freeze-dried medium were stored in a container with a desiccant.

One loopful of the test bacteria was removed from an agar plate and suspended in 4.5 mls. of sterile saline.

The microtubes were inoculated with 1.0 ml. of the suspension, then sealed with a rubber stopper and placed in a labeled rack with a white background. This process was repeated for each carbohydrate used.

All the tubes were placed in an incubator at 37°C. and inspected at 1, 2, 3, 4, 5, 6 and 24 hours. A change in color from alkaline (red) to acid (yellow) is indicative of fermentation.

The following tables indicate the results. In each table the following notations are used:
− = negative (red color)
± = changing to positive (orange color)
+ = positive (yellow color)

As a control BBL Phenol Red Broth Base (Baltimore Biological Laboratories) with appropriate carbohydrates was used. The broth was inoculated with the same inoculum as in the test media. The results shown are those after 24 hours incubation and shows the correlation of the test system of this invention with the conventional test systems.

ORGANISM

| Carbohydrate | Arizona arizonae 501 Hours Incubation | | | | | | | Control Broth |
|---|---|---|---|---|---|---|---|---|
| | 1 | 2 | 3 | 4 | 5 | 6 | 24 | |
| Dextrose | + | + | + | + | + | + | + | + |
| Lactose | − | − | − | − | − | − | − | − |
| Sucrose | − | − | − | − | − | − | − | − |
| Mannitol | − | + | + | + | + | + | + | + |
| Dulcitol | − | − | − | − | − | − | − | − |
| Salicin | − | − | − | − | − | − | − | − |
| Adonitol | − | − | − | − | − | − | − | − |
| Inositol | − | − | − | − | − | − | − | − |
| Sorbitol | − | ± | ± | + | + | + | + | + |
| Arabinose | − | ± | + | + | + | + | + | + |
| Raffinose | − | − | − | − | − | − | − | − |
| Rhamnose | − | + | + | + | + | + | + | + |

Results were complete in 3 hours

ORGANISM

| Carbohydrate | Edwardsiella tarda Hours Incubation | | | | | | | Control Broth |
|---|---|---|---|---|---|---|---|---|
| | 1 | 2 | 3 | 4 | 5 | 6 | 24 | |
| Dextrose | − | + | + | + | + | + | + | + |
| Lactose | − | − | − | − | − | − | − | − |
| Sucrose | − | − | − | − | − | − | − | − |
| Mannitol | − | − | − | − | − | − | − | − |
| Dulcitol | − | − | − | − | − | − | − | − |
| Salicin | − | − | − | − | − | − | − | − |
| Adonitol | − | − | − | − | − | − | − | − |
| Inositol | − | − | − | − | − | − | − | − |
| Sorbitol | − | − | − | − | − | − | − | − |
| Arabinose | − | − | − | ± | + | + | + | + |
| Raffinose | − | − | − | − | − | − | − | − |

ORGANISM-continued

Edwardsiella tarda

| Carbohydrate | 1 | 2 | 3 | 4 | 5 | 6 | 24 | Control Broth |
|---|---|---|---|---|---|---|---|---|
| Rhamnose | − | − | − | − | − | − | − | − |

Results were complete in 5 hours

ORGANISM

Escherichia coli 11775

| Carbohydrate | 1 | 2 | 3 | 4 | 5 | 6 | 24 | Control Broth |
|---|---|---|---|---|---|---|---|---|
| Dextrose | + | + | + | + | + | + | + | + |
| Lactose | + | + | + | + | + | + | + | + |
| Sucrose | − | − | − | − | − | − | − | − |
| Mannitol | + | + | + | + | + | + | + | + |
| Dulcitol | − | − | − | − | − | − | − | − |
| Salicin | − | − | − | − | − | − | − | − |
| Adonitol | − | − | − | − | − | − | − | − |
| Inositol | − | − | − | − | − | − | − | − |
| Sorbitol | + | + | + | + | + | + | + | + |
| Arabinose | + | + | + | + | + | + | + | + |
| Raffinose | − | − | − | − | − | − | − | − |
| Rhamnose | + | + | + | + | + | + | + | + |

Results were complete in 1 hour

ORGANISM

Enterobacter aerogenes 50363

| Carbohydrate | 1 | 2 | 3 | 4 | 5 | 6 | 24 | Control Broth |
|---|---|---|---|---|---|---|---|---|
| Dextrose | ± | + | + | + | + | + | + | + |
| Lactose | ± | + | + | + | + | + | + | + |
| Sucrose | − | − | − | − | − | − | − | − |
| Mannitol | ± | + | + | + | + | + | + | + |
| Dulcitol | − | − | − | − | − | − | − | − |
| Salicin | − | − | − | − | − | − | − | − |
| Adonitol | − | − | ± | + | + | + | + | + |
| Inositol | − | − | − | − | − | + | + | + |
| Sorbitol | ± | + | + | + | + | + | + | + |
| Arabinose | ± | + | + | + | + | + | + | + |
| Raffinose | ± | + | + | + | + | + | + | + |
| Rhamnose | − | + | + | + | + | + | + | + |

Inositol took more than 6 hours to ferment.

ORGANISM

Enterobacter cloacae 50358B

| Carbohydrate | 1 | 2 | 3 | 4 | 5 | 6 | 24 | Control Broth |
|---|---|---|---|---|---|---|---|---|
| Dextrose | + | + | + | + | + | + | + | + |
| Lactose | + | + | + | + | + | + | + | + |
| Sucrose | + | + | + | + | + | + | + | + |
| Mannitol | − | + | + | + | + | + | + | + |
| Dulcitol | − | − | − | − | − | − | − | − |
| Salicin | − | + | + | + | + | + | + | + |
| Adonitol | − | − | − | − | ± | + | + | + |
| Inositol | − | − | − | − | + | + | − | − |
| Sorbitol | − | + | + | + | + | + | + | + |
| Arabinose | + | + | + | + | + | + | + | + |
| Raffinose | ± | + | + | + | + | + | + | + |
| Rhamnose | − | + | + | + | + | + | + | + |

Inositol took more than 6 hours to ferment.

ORGANISM

Klebsiella pneumoniae 8047

| Carbohydrate | 1 | 2 | 3 | 4 | 5 | 6 | 24 | Control Broth |
|---|---|---|---|---|---|---|---|---|
| Dextrose | ± | + | + | + | + | + | + | + |
| Lactose | − | − | − | − | − | − | − | − |
| Sucrose | − | + | + | + | + | + | + | + |
| Mannitol | − | + | + | + | + | + | + | + |
| Dulcitol | − | − | − | − | − | − | − | − |
| Salicin | − | + | + | + | + | + | + | + |
| Adonitol | − | − | − | ± | + | + | + | + |
| Inositol | − | − | − | − | − | − | + | + |
| Sorbitol | − | ± | + | + | + | + | + | + |
| Arabinose | − | − | ± | ± | + | + | + | + |
| Raffinose | − | − | − | − | − | + | + | + |
| Rhamnose | − | − | ± | + | + | + | + | + |

Inositol and Raffinose took more than 6 hours to ferment.

ORGANISM

Proteus mirabilis 15146

| Carbohydrate | 1 | 2 | 3 | 4 | 5 | 6 | 24 | Control Broth |
|---|---|---|---|---|---|---|---|---|
| Dextrose | − | ± | + | + | + | + | + | + |
| Lactose | − | − | − | − | − | − | − | − |
| Sucrose | − | − | − | − | − | − | − | − |
| Mannitol | − | − | − | − | − | − | − | − |
| Dulcitol | − | − | − | − | − | − | − | − |
| Salicin | − | − | − | − | − | − | − | − |
| Adonitol | − | − | − | − | − | − | − | − |
| Inositol | − | − | − | − | − | − | − | − |
| Sorbitol | − | − | − | − | − | − | − | − |
| Arabinose | − | − | − | − | − | − | − | − |
| Raffinose | − | − | − | − | − | − | − | − |
| Rhamnose | − | − | − | − | − | − | − | − |

Results were complete within 3 hours

ORGANISM

Providencia alcalifaciens

| Carbohydrate | 1 | 2 | 3 | 4 | 5 | 6 | 24 | Control Broth |
|---|---|---|---|---|---|---|---|---|
| Dextrose | − | + | + | + | + | + | + | + |
| Lactose | − | − | − | − | − | − | − | − |
| Sucrose | − | − | − | − | − | − | − | − |
| Mannitol | − | − | − | − | − | − | − | − |
| Dulcitol | − | − | − | − | − | − | − | − |
| Salicin | − | − | − | − | − | − | − | − |
| Adonitol | − | − | − | − | − | − | + | + |
| Inositol | − | − | − | − | − | − | − | − |
| Sorbitol | − | − | − | − | − | − | − | − |
| Arabinose | − | − | − | − | − | − | − | − |
| Raffinose | − | − | − | − | − | − | − | − |
| Rhamnose | − | − | − | − | − | − | − | − |

Adonitol took more than 6 hours to ferment

ORGANISM

Salmonella newport

| Carbohydrate | 1 | 2 | 3 | 4 | 5 | 6 | 24 | Control Broth |
|---|---|---|---|---|---|---|---|---|
| Dextrose | − | + | + | + | + | + | + | + |
| Lactose | − | − | − | − | − | − | − | − |
| Sucrose | − | − | − | − | − | − | − | − |
| Mannitol | − | + | + | + | + | + | + | + |
| Dulcitol | − | + | + | + | + | + | + | + |
| Salicin | − | − | − | − | − | − | − | − |
| Adonitol | − | − | − | − | − | − | − | − |
| Inositol | − | − | − | − | − | − | − | − |
| Sorbitol | − | ± | ± | + | + | + | + | + |
| Arabinose | − | ± | + | + | + | + | + | + |
| Raffinose | − | − | − | − | − | − | − | − |
| Rhamnose | − | + | + | + | + | + | + | + |

Results were complete within 4 hours

ORGANISM

Shigella dysenteriae

| Carbohydrate | 1 | 2 | 3 | 4 | 5 | 6 | 24 | Control Broth |
|---|---|---|---|---|---|---|---|---|
| Dextrose | − | + | + | + | + | + | + | + |
| Lactose | − | − | − | − | − | − | − | − |
| Sucrose | − | − | − | − | − | − | − | − |
| Mannitol | − | − | − | − | − | − | − | − |
| Dulcitol | − | − | − | − | − | − | − | − |
| Salicin | − | − | − | − | − | − | − | − |
| Adonitol | − | − | − | − | − | − | − | − |
| Inositol | − | − | − | − | − | − | − | − |

ORGANISM-continued

| Carbohydrate | *Shigella dysenteriae* Hours Incubation | | | | | | | Control Broth |
|---|---|---|---|---|---|---|---|---|
| | 1 | 2 | 3 | 4 | 5 | 6 | 24 | |
| Sorbitol | − | − | − | − | − | − | − | − |
| Arabinose | − | − | − | − | − | − | − | − |
| Raffinose | − | − | − | − | − | − | − | − |
| Rhamnose | − | − | + | + | + | + | + | + |

Results were complete within 3 hours

EXAMPLE 2

Standard carbohydrate media were prepared containing the following ingredients on a weight basis:

| | |
|---|---|
| 0.5% | trypticase peptone |
| 1% | carbohydrate |
| 0.0018% | phenol red indicator |
| 100 ml. | water q.s. |
| | adjusted to pH 7.8 with 10% NaOH |

The ingredients for the broth media were mixed at room temperature then autoclaved at 118°C. for 15 minutes. After cooling, 0.1 ml. quantities of the medium was pipetted into a row of micro wells in a micro titer tray. The trays filled with media were placed in a freeze-dryer chamber preset at −40°F. The chamber was evacuated until a vacuum of about 100 microns or less was achieved. The chamber was then heated to 70°F. for about 24 hours. The vacuum was broken and the trays were removed. Each well was then sealed with plastic tape.

The following organisms, plated on TSA plates were incubated at 38°C. for 24 hours:

1. Arizona hinshawii 1925-66
2. coli 0126
3. E. coli ATCC 11775
4. E. hafniae ATCC 13337
5. E. cloacae ATCC 13047
6. E. tarda ATCC 15469
7. K. pneumoniae ATCC 8047
8. P. vulgaris ATCC 6380
9. S. flexneri LA
10. S. typhimurium ATCC 13311
11. S. newport
12. S. marcescens 5966

A loopful of each organism was suspended in 2 ml. of distilled water. 0.1 ml. of the suspension was then injected with a needle and syringe into each micro well containing the freeze dried media. A series of eight wells of each carbohydrate were inoculated with each organism. The trays were then incubated at 38°C. and inspected at 1, 2, 3, 4, 5, 6 and 24 hours. A change in color from alkaline (red) to acid (yellow) is indicative of fermentation.

The reaction in the micro tray well were clear and distinct.

The following tables indicate the results. In the tables the following notations are used:

+ = positive
− = negative
± = changing from negative to positive

MICRO-PLATE TECHNIQUE

| Carbohydrate | Organism *Arizona hinshawii* 1925–66 Hours Incubation | | | | Media Broth | |
|---|---|---|---|---|---|---|
| | 1 | 2 | 3 | 4 | 5 | 6 |
| Dextrose | + | + | + | + | + | + |
| Lactose | − | − | − | − | − | − |
| Sucrose | − | − | − | − | − | − |
| Mannitol | + | + | + | + | + | + |
| Dulcitol | − | − | − | − | − | − |
| Inositol | − | − | − | − | − | − |
| Sorbitol | − | − | ± | + | + | + |
| Raffinose | − | − | − | − | − | − |

MICRO-PLATE TECHNIQUE

| Carbohydrate | Organism *Escherichia coli* 11775 Hours Incubation | | | | Media Broth | |
|---|---|---|---|---|---|---|
| | 1 | 2 | 3 | 4 | 5 | 6 |
| Dextrose | ± | + | + | + | + | + |
| Lactose | − | + | + | + | + | + |
| Sucrose | − | − | − | − | − | − |
| Mannitol | − | + | + | + | + | + |
| Dulcitol | − | − | − | − | − | − |
| Inositol | − | − | − | − | − | − |
| Sorbitol | − | − | ± | + | + | + |
| Raffinose | − | − | − | − | − | − |

MICRO-PLATE TECHNIQUE

| Carbohydrate | Organism *E. coli* 0126 Hours Incubation | | | | Media Broth | |
|---|---|---|---|---|---|---|
| | 1 | 2 | 3 | 4 | 5 | 6 |
| Dextrose | + | + | + | + | + | + |
| Lactose | − | + | + | + | + | + |
| Sucrose | − | − | − | + | + | + |
| Mannitol | + | + | + | + | + | + |
| Dulcitol | − | − | − | − | − | − |
| Inositol | − | − | − | − | − | − |
| Sorbitol | − | − | − | − | − | − |
| Raffinose | − | − | ± | + | + | + |

MICRO-PLATE TECHNIQUE

| Carbohydrate | Organism *Edwardsiella tarda* 15469 Hours Incubation | | | | Media Broth | |
|---|---|---|---|---|---|---|
| | 1 | 2 | 3 | 4 | 5 | 6 |
| Dextrose | ± | + | + | + | + | + |
| Lactose | − | − | − | − | − | − |
| Sucrose | − | − | − | − | − | − |
| Mannitol | − | − | − | − | − | − |
| Dulcitol | − | − | − | − | − | − |
| Inositol | − | − | − | − | − | − |
| Sorbitol | − | − | − | − | − | − |
| Raffinose | − | − | − | − | − | − |

MICRO-PLATE TECHNIQUE

| Carbohydrate | Organism *Enterobacter hafniae* 13337 Hours Incubation | | | | Media Broth | |
|---|---|---|---|---|---|---|
| | 1 | 2 | 3 | 4 | 5 | 6 |
| Dextrose | − | + | + | + | + | + |
| Lactose | − | − | − | − | − | − |
| Sucrose | − | − | − | − | − | − |
| Mannitol | − | − | − | − | ± | ± |
| Dulcitol | − | − | − | − | − | − |
| Inositol | − | − | − | − | − | − |
| Sorbitol | − | − | − | − | − | − |
| Raffinose | − | − | − | − | − | − |

MICRO-PLATE TECHNIQUE

| Organism<br>E. cloacae 13047<br>Carbohydrate | Media<br>Broth<br>Hours Incubation | | | | | |
|---|---|---|---|---|---|---|
| | 1 | 2 | 3 | 4 | 5 | 6 |
| Dextrose | + | + | + | + | + | + |
| Lactose | + | + | + | + | + | + |
| Sucrose | + | + | + | + | + | + |
| Mannitol | − | + | + | + | + | + |
| Dulcitol | − | − | − | − | − | − |
| Inositol | − | − | − | − | − | − |
| Sorbitol | − | ± | + | + | + | + |
| Raffinose | − | ± | + | + | + | + |

MICRO-PLATE TECHNIQUE

| Organism<br>Klebsiella pneumoniae 8047<br>Carbohydrate | Media<br>Broth<br>Hours Incubation | | | | | |
|---|---|---|---|---|---|---|
| | 1 | 2 | 3 | 4 | 5 | 6 |
| Dextrose | + | + | + | + | + | + |
| Lactose | − | − | − | − | − | − |
| Sucrose | − | + | + | + | + | + |
| Mannitol | − | + | + | + | + | + |
| Dulcitol | − | − | − | − | − | − |
| Inositol | − | − | − | − | ± | ± |
| Sorbitol | − | − | + | + | + | + |
| Raffinose | − | − | − | − | ± | + |

MICRO-PLATE TECHNIQUE

| Organism<br>Proteus vulgaris 6380<br>Carbohydrate | Media<br>Broth<br>Hours Incubation | | | | | |
|---|---|---|---|---|---|---|
| | 1 | 2 | 3 | 4 | 5 | 6 |
| Dextrose | − | ± | + | + | + | + |
| Lactose | − | − | − | − | − | − |
| Sucrose | − | + | + | + | + | + |
| Mannitol | − | − | − | − | − | − |
| Dulcitol | − | − | − | − | − | − |
| Inositol | − | − | − | − | − | − |
| Sorbitol | − | − | − | − | − | − |
| Raffinose | − | − | − | − | − | − |

MICRO-PLATE TECHNIQUE

| Organism<br>Salmonella newport<br>Carbohydrate | Media<br>Broth<br>Hours Incubation | | | | | |
|---|---|---|---|---|---|---|
| | 1 | 2 | 3 | 4 | 5 | 6 |
| Dextrose | + | + | + | + | + | + |
| Lactose | − | − | − | − | − | − |
| Sucrose | − | − | − | − | − | − |
| Mannitol | − | − | − | + | + | + |
| Dulcitol | − | − | − | − | − | − |
| Inositol | − | − | − | − | − | − |
| Sorbitol | − | − | − | − | ± | + |
| Raffinose | − | − | − | − | − | − |

MICRO-PLATE TECHNIQUE

| Organism<br>Shigella flexneri<br>Carbohydrate | Media<br>Broth<br>Hours Incubation | | | | | |
|---|---|---|---|---|---|---|
| | 1 | 2 | 3 | 4 | 5 | 6 |
| Dextrose | − | ± | ± | ± | + | + |
| Lactose | − | − | − | − | − | − |
| Sucrose | − | − | − | − | − | − |
| Mannitol | − | − | − | − | ± | ± |
| Dulcitol | − | − | − | − | − | − |
| Inositol | − | − | − | − | − | − |
| Sorbitol | − | − | − | − | − | − |
| Raffinose | − | − | − | − | − | − |

MICRO-PLATE TECHNIQUE

| Organism<br>Serratia marcescens 5966<br>Carbohydrate | Media<br>Broth<br>Hours Incubation | | | | | |
|---|---|---|---|---|---|---|
| | 1 | 2 | 3 | 4 | 5 | 6 |
| Dextrose | + | + | + | + | + | + |
| Lactose | − | − | − | − | − | − |
| Sucrose | − | + | + | + | + | + |
| Mannitol | − | − | − | + | + | + |
| Dulcitol | − | − | − | − | − | − |
| Inositol | − | − | − | − | + | − |
| Sorbitol | − | − | − | − | + | + |
| Raffinose | − | − | − | − | − | + |

EXAMPLE 3

Broth medium was prepared containing the following ingredients on a weight basis:

| Ingredient | g/100 ml. |
|---|---|
| Ortho-nitrophenyl-beta-D-galaciopyranomide (ONPG) | 0.05 |
| Trypitcase peptene | 10.0 |
| Distilled water | 100.0 ml. |

The ingredients were dissolved mixing together and heating to 60°C. The solution was allowed to cool to room temperature and then adjusted to pH 7.4 with a fresh solution of 10% w/v NaOH. The resulting solution was sterilized by filtration through a 0.22 micron nalgene filter.

0.1 Ml. of the resulting ONPG medium was put into 10 × 75 mm. sterile glass tubes under a laminar flow hood. The tubes were then capped with rubber stoppers. The tubes were placed in an aluminum template and placed a freeze-dryer chamber preset at −40°F. After one hour at −40°F., the chamber was evacuated until a vacuum of about 100 microns or less was achieved. The samples are then dried for 48 hours with the freezer turned off. The tubes are then removed.

The following organisms were tested:

| 1. | S. typhimurium | ATCC 13311 |
| 2. | S. typhi | SC 10 |
| 3. | S. paratyphi B | |
| 4. | Arizona hinshawii | 1925–66 |
| 5. | Citrobacter sp. | 3171–59 |
| 6. | E. hafnia | ATCC 13337 |
| 7. | P. vulgaris | ATCC 6380 |
| 8. | E. coli | 0127a: B8 |

Each stock culture was subcultured to a Trypticase Soy Agar plate, one organism per plate and incubated at 35°–37°C. for 24 hours.

One loopful of the test bacteria was removed and transferred to a tube containing 5 ml. of sterile saline and mixed.

The micro tubes were inoculated with 1 ml. of the suspension then sealed with a rubber stopper.

This was repeated for each organism.

All the tubes were incubated at 35°–37°C. for 18–24 hours. Positive results must be incubated the full 18–24 hours to confirm that they are negative.

A positive result is manifested by a bright yellow color while no color develops when the results are negative.

| Organism | ONPG Medium |
|---|---|
| S. typhimurium | − |

-continued

| Organism | ONPG Medium |
| --- | --- |
| S. typhi | − |
| S. paratyphi B | − |
| Arizona hinshawii | + |
| Citrobacter sp. | + |
| E. hafniae | + |
| P. Vulgaris | − |
| E. coli | + |

I claim:

1. A method for identifying Enterobacteriaceae consisting essentially of (a) sterilizing and lyophilizing, in separate microcontainers, a series of liquid nutrient broth media containing an indicator, (b) forming liquid culture media in said microcontainers by adding 0.1 to 1 ml. of an aqueous mixture of an unidentified member of Enterobacteriaceae directly to each of said series of sterile, lyophilized nutrient broth media in separate microcontainers, (c) incubating each of said series of nutrient broth media at about 35° to 38°C., (d) observing and comparing the incubation results to a predetermined fermentation, growth or enzyme activity profile to thereby identify said unidentified member of Enterobacteriaceae.

2. The method of claim 1 wherein said indicator is a color indicator.

3. The method of claim 1 wherein each nutrient broth medium is different and, before lyophilization, is at pH 7.3 to 7.8 and consists of, on a weight basis per 100 ml., 0.5% trypticase peptone, 1% of a carbohydrate, 0.0018% phenol red indicator and sufficient water to make 100 ml.

4. The method of claim 1 wherein a single broth medium is used and is, before lyophilization, at pH 7.4 and consists of, on a weight basis per 100 ml., 0.5 grams ortho-nitrophenylbeta-D-galactopyranoside, 10 grams trypticase peptone, and 100 ml. water.

5. The method of claim 1 wherein the nutrient medium is contained in a micro titer tray.

* * * * *

UNITED STATES PATENT AND TRADEMARK OFFICE
CERTIFICATE OF CORRECTION

PATENT NO. : 3,951,747
DATED : April 20, 1976
INVENTOR(S) : Patrick Michael Yananton It is certified that error appears in the above-identified patent and that said Letters Patent are hereby corrected as shown below:

Title Page, No. [56] under References Cited delete

Lettau Zeit. Chem., 1970, Vol. 10, Heft. 12, pp.462.

Column 10, line 21, Example 3, "-D-galaciopyranomide" should be

-D-galactopyranoside

Column 10, line 22, Example 3, "peptene" should be peptone

Column 12, line 17, claim 4, "ortho-nitrophenylbeta-D-" should be ortho-nitrophenyl-beta-D-

*Signed and Sealed this*

*twenty-ninth* Day of *June 1976*

[SEAL]

*Attest:*

RUTH C. MASON
*Attesting Officer*

C. MARSHALL DANN
*Commissioner of Patents and Trademarks*